US006401714B1

(12) United States Patent
Giorgini

(10) Patent No.: US 6,401,714 B1
(45) Date of Patent: Jun. 11, 2002

(54) SELF CONTAINED BREATHING APPARATUS

(75) Inventor: Eugene Giorgini, Cheektowaga, NY (US)

(73) Assignee: Scott Technologies, Inc., Cleveland, OH (US)

( * ) Notice: Subject to any disclaimer, the term of this patent is extended or adjusted under 35 U.S.C. 154(b) by 0 days.

(21) Appl. No.: 09/284,103

(22) PCT Filed: Mar. 27, 1998

(86) PCT No.: PCT/US98/06158

§ 371 (c)(1),
(2), (4) Date: Apr. 7, 1999

(87) PCT Pub. No.: WO98/43705

PCT Pub. Date: Oct. 8, 1998

Related U.S. Application Data

(60) Provisional application No. 60/041,955, filed on Apr. 3, 1997.

(51) Int. Cl.[7] .......... A61M 16/00

(52) U.S. Cl. .......... 128/204.26; 128/204.29; 128/202.22

(58) Field of Search .......... 128/204.26, 204.29, 128/202.22, 204.22; 137/908

(56) References Cited

U.S. PATENT DOCUMENTS

| | | | | | |
|---|---|---|---|---|---|
| 2,420,375 | A | * | 5/1947 | Huggenberger | 137/153 |
| 3,067,760 | A | * | 12/1962 | Haverland et al. | 137/63 |
| 3,362,404 | A | * | 1/1968 | Beasley | 128/145.8 |
| 3,481,356 | A | * | 12/1969 | McQueen | 137/110 |
| 3,508,542 | A | * | 4/1970 | Browner | 128/142.2 |
| 3,805,780 | A | * | 4/1974 | Cramer et al. | 128/142.2 |
| 3,957,044 | A | * | 5/1976 | Fletcher et al. | 128/142.2 |
| 4,240,419 | A | * | 12/1980 | Furlong et al. | 128/204.23 |
| 4,289,126 | A | * | 9/1981 | Seireg et al. | 128/204.24 |
| 4,667,670 | A | * | 5/1987 | Feathers | 128/204.26 |
| 4,793,340 | A | * | 12/1988 | Ottestad | 128/200.24 |
| 4,821,767 | A | * | 4/1989 | Jackson | 137/491 |
| 4,889,115 | A | * | 12/1989 | Bozano | 128/204.26 |
| 5,464,009 | A | * | 11/1995 | Tatarek-Gintowt | 128/205.24 |
| 5,503,140 | A | * | 4/1996 | Winefordner et al. | 128/200.29 |
| 5,724,961 | A | * | 3/1998 | Tistrand | 128/205.24 |
| 5,787,882 | A | * | 8/1998 | Hamilton | 128/204.26 |
| 5,803,073 | A | * | 9/1998 | Toth | 128/205.24 |
| 5,839,436 | A | * | 11/1998 | Fangrow, Jr. et al. | 128/205.24 |
| 5,911,220 | A | * | 6/1999 | Morgan et al. | 128/205.24 |

* cited by examiner

*Primary Examiner*—John G. Weiss
*Assistant Examiner*—Mital Patel
(74) *Attorney, Agent, or Firm*—Ralph E. Jocke; Daniel D. Wasil; Walker & Jocke

(57) ABSTRACT

A self contained breathing apparatus includes a pressure vessel which holds a supply of breathing air. The pressure vessel is in fluid communication through a first stage pressure regulator with a second stage breathing regulator. The breathing regulator is operatively connected to a user face mask. When the pressure available in the supply is at a suitable pressure, the pressure regulator provides pressure to breathing regulator at a first pressure. When the pressure in the supply falls to a value indicative of impending depletion of the air supply, a transfer piston in a step up vale shifts. A change in condition of the step up valve causes a step up piston to increase the output pressure from regulator. This increased pressure moves a sensing piston and causes indicating devices in an alarm circuit to be activated. In alternative embodiments, an electronic alarm module may be used.

27 Claims, 4 Drawing Sheets

SELF CONTAINED BREATHING APPARATUS

This application is the National Stage of International Application No. PCT/US98/06158, filed Mar. 27, 1998, which claims the benefit of U.S. Provisional Application No. 60/041,955, filed Apr. 3, 1997.

TECHNICAL FIELD

This invention relates to a self contained breathing apparatus.

Specifically this invention relates to a self contained breathing apparatus that provides an indication to a user that a supply of air is approaching depletion.

BACKGROUND ART

Self contained breathing apparatus are known in the prior art. Such devices are commonly used by individuals who are required to perform activities in noxious atmospheres. Individuals who commonly use self contained breathing apparatus include fire fighters and persons involved in cleaning up chemical spills.

A self contained breathing apparatus generally includes a supply of pressurized breathing air. The breathing air is maintained in a vessel at a relatively high pressure. Air flows from the pressure vessel to a first stage regulator which reduces the pressure from the high pressure within the vessel to a lower pressure. Air from the primary regulator is communicated to a second stage regulator. The second stage regulator is generally in communication with a face mask, hood or similar device worn by a user. The second stage regulator operates to deliver air into the face mask or hood in response to a user's inhalation. The second stage regulator often stops the flow of air into the face mask while the user is exhaling. In this way the air supply is conserved.

A pressure vessel can supply breathing air to a user for only a limited duration. It is often desirable to warn a user that the air supply is approaching depletion so that they may leave the area with the noxious atmosphere before the supply is depleted. My prior patent, U.S. Pat. No. 3,957,044, discloses such a system. In my prior system a pair of first stage regulators set at substantially different pressures are used to supply air to a second stage regulator mounted on a user's face mask. A pair of transfer valves are connected to the first stage regulators and to the line which supplies the second stage regulator.

In accordance with my previously developed system, when the supply of air in the pressure vessel is above a pressure which is indicative of impending depletion, the transfer valves are automatically positioned to supply air to the second stage regulator through the primary first stage regulator which is set at a first nominal pressure. However, when the pressure in the pressure vessel falls to a level which indicates that depletion of the supply is approaching, the transfer valves automatically shift so that the second stage regulator is supplied with air from the other first stage regulator which is set at a higher, second pressure. This higher pressure is sufficient to actuate an alarm device, such as a whistle or vibrating alarm device which warns the user of the impending depletion of the air supply in the pressure vessel each time the user inhales.

While my prior system is highly reliable, the use of two first stage regulators and a pair of transfer valves adds to its cost. In addition, it would be desirable to provide additional forms of warnings to a user of the impending depletion of the supply of air in the pressure vessel. This is particularly desirable for users who must work in noisy environments in which a whistle or other auditory or vibratory warning indication may not be perceived. Alternatively, an individual with a hearing impairment may benefit by having a visual or other form of indication in addition to an audible warning.

Thus there exists a need for a self contained breathing apparatus that provides a user with an indication of the impending depletion of the air supply, which provides multiple types of indications and which is more economical than prior systems.

DISCLOSURE OF INVENTION

It is an object of the present invention to provide a self contained breathing apparatus.

It is a further object of the present invention to provide a regulator for use in connection with a self contained breathing apparatus.

It is a further object of the present invention to provide a self contained breathing apparatus which provides a user with an indication that an air supply is approaching depletion.

It is a further object of the present invention to provide a self contained breathing apparatus that provides a user with multiple indications of the impending depletion of an air supply.

It is a further object of the present invention to provide a self contained breathing apparatus that is more economical to manufacture and use.

Further objects of the present invention will be made apparent in the following Best Modes for Carrying Out Invention and the appended claims.

The foregoing objects are accomplished in a preferred embodiment of the present invention by a self contained breathing apparatus that includes a pressure vessel containing a supply of breathing air. The breathing air from the pressure vessel is communicated to a first stage pressure regulator which is initially set at a nominal first pressure value. The pressure from the pressure vessel is also communicated to a step up valve. The first stage regulator delivers air at the first pressure to a second stage breathing regulator mounted on a face mask worn by a user. Air is then supplied to the face mask through the breathing regulator in response to a user's breathing efforts.

When the pressure in the pressure vessel is above a level indicative of impending depletion, a transfer piston in the step up valve is biased by the pressure from the pressure vessel to a closed position. When the pressure in the pressure vessel falls to a level indicative of impending depletion, the pressure acting on the transfer piston in the step up valve is reduced to a level which causes the transfer piston to shift to a second position. Movement of the transfer piston causes pressure from the first stage regulator to be delivered to a charging passage. Delivery of increased pressure to the charging passage moves a step up piston which acts to change the pressure setting of the first stage regulator to a higher pressure. This increased pressure is communicated to the second stage breathing regulator.

The air supply to the second stage regulator is in fluid communication with a sensor which may be adjacent to the face mask or in another location. The increase in pressure is detected by the sensor which actuates an alarm circuit. The alarm circuit may include visual alarms such as lights, as well as audio or other alarms which provide the user with an indication of the impending depletion of the air supply. In addition, the increased pressure may also be used to actuate a whistle or vibrator of the conventional type in the mask or other location. These multiple alarm indications provide greater assurance that the user will be aware of the impending depletion of the air supply even though the user is working in a noisy or other difficult environment.

BEST MODES FOR CARRYING OUT INVENTION

Figure 1:
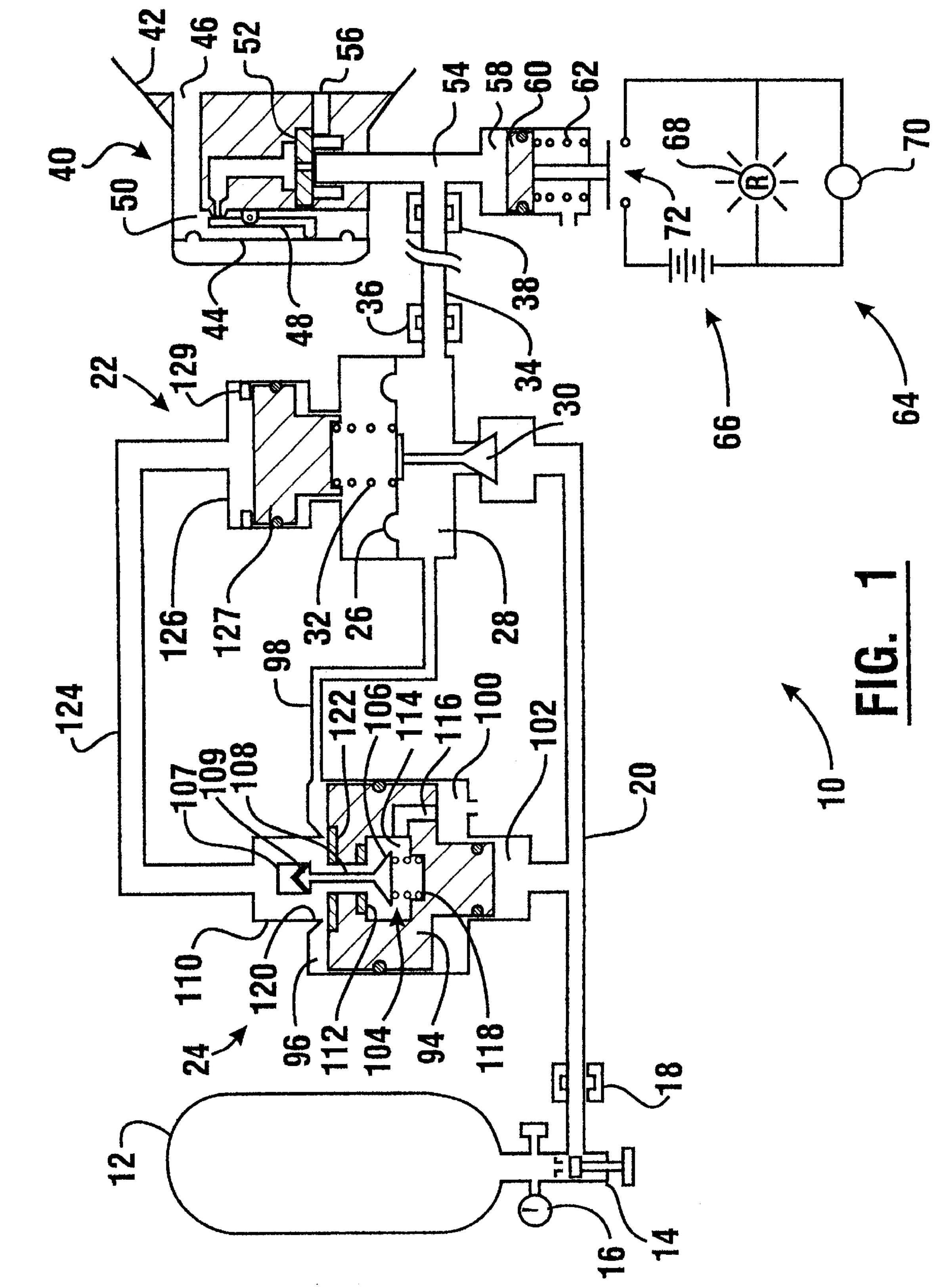
FIG. 1 is a schematic view of a self contained breathing apparatus of one preferred embodiment of the present invention which is used to deliver air to a user, and in which the air supply is above a level indicative of impending depletion.

Referring now to the drawings and particularly to FIG. 1, there is shown therein a first embodiment of a self contained breathing apparatus of the present invention generally indicated 10. The apparatus includes a pressure vessel 12 or other source which provides a supply of breathing air. In one preferred form of the invention the pressure vessel may be of the type that initially holds air at a pressure of about 316.4 Kg./sq.cm (4500 PSIG). The pressure vessel includes a conventional outlet valve 14 and a pressure gauge 16. The pressure vessel 12 is preferably coupled to the remainder of the system through a releasable coupling 18.

Coupling 18 is connected to a supply conduit, schematically indicated 20. Supply conduit 20 is in fluid communication with a first stage pressure regulator 22. Supply conduit 20 is also in fluid communication with a step up valve 24.

First stage regulator 22 in the embodiment shown is a single stage regulator. It includes a diaphragm 26 which serves as a movable member which is acted upon by fluid pressure in a regulator chamber 28. Flow into regulator chamber 28 is controlled in response to the position of a member or metering element 30. Diaphragm 26 is also acted upon by a bias spring 32, the force of which acts in a direction opposite to the force applied to the diaphragm by the regulator pressure in chamber 28. In the condition shown in FIG. 1, the force of the bias spring is preferably set so that the fluid pressure maintained in chamber 28 is generally about 7.03 Kg./sq.cm (100 PSIG).

Chamber 28 is in fluid communication through an outlet with a hose 34. This hose is preferably a flexible resilient conduit suitable for transfer of the air within the range of pressures discussed herein. Hose 34 is operatively connected to the regulator 22 through a coupling 36.

A breathing regulator 40 is in fluid communication with hose 34 through a coupling 38. Breathing regulator 40 serves as a second stage pressure regulator for supplying air to a user (not shown). Breathing regulator 40 is in operative connection with a face mask 42 which is preferably in fluid tight relation with the user's mouth and nose.

Breathing regulator 40 may be any one of a number of conventional or novel types including demand type regulators or positive pressure type regulators. It should be understood that the present invention is in no way limited to a particular type of regulator for supplying air to a user.

In FIG. 1 a pilot actuated demand type regulator is schematically indicated. This regulator includes a moveable sensing diaphragm 44 which moves in response to pressure that is applied to the diaphragm as a result of a user's breathing efforts. The pressure fluctuations caused by the user's breathing is transmitted through a sensing passage 46 to the chamber which is bounded by diaphragm 44. Negative pressure acting on the diaphragm moves a lever 48. Rotational movement of lever 48 in a counter clockwise direction, as shown in FIG. 1, opens a pilot 50. The opening of pilot 50 causes an element in a main valve 52 to deform and to open the flow of air from a regulator supply passage 54 to a delivery passage 56 located in the interior of the mask.

In the regulator embodiment shown, an increase in pressure in the mask as a result of a user's exhalation moves diaphragm 44 in a manner which causes lever 48 to close pilot 50. Lever 48 is preferably biased to move the lever to a position closing pilot 50. The closing of the pilot causes main valve 52 to close, stopping the delivery of air to the mask through delivery passage 56. As pressure in the mask rises in response to a user's exhalation, a separate exhalation valve (not shown) opens in response to the pressure increase and releases air from the mask 42.

In a preferred embodiment of the invention, breathing regulator 40 includes therein additional devices which are not shown. Such additional devices may include for example devices or mechanisms which enable the regulator to operate at a positive pressure so as to avoid the infiltration of contaminants into the mask. An example of a regulator having mechanisms which enable operation at a positive pressure are shown in International Publication Number WO97/46281 dated Dec. 11, 1997 the disclosure of which is incorporated herein by reference. Breathing regulator 40 also preferably includes or is operatively connected with conventional or novel type warning devices such as a valve and whistle combination or a vibration device which provides an audible or vibration type indication responsive to the pressure in supply passage 54 exceeding a predetermined level. In one preferred form of the invention these devices are set to begin providing an alarm indication at approximately 9.14 Kg./sq.cm (130 PSIG).

Hose 34 is also in communication with a sensing chamber 58. Sensing chamber 58 has a sensing piston 60 movably mounted therein. Sensing piston 60 is biased by a spring 62.

Sensing piston 60 is in operative connection with an alarm circuit generally indicated 64. Alarm circuit 64 includes a battery or other power source 66. Alarm circuit 64 also includes a light emitter 68 and an alternative warning device 70. Warning device 70 may include for example, a piezoelectric sound emitter or other type of electrically actuated visual, audio or vibratory alarm device.

Movement of sensing piston 60 responsive to increased pressure in sensing chamber 58 closes switch contacts 72. The closing of switch contacts 72 completes the circuit to actuate light emitter 68 and warning device 70. In one preferred form of the invention, sensing piston 60 is operative to close switch contacts 72 at generally the same increased pressure which actuates the other conventional or unconventional audible or vibratory warning devices in connection with breathing regulator 40.

It should be understood that in a preferred embodiment of the present invention light emitter 68 and warning device 70 are preferably positioned to be visible or otherwise perceptible by a user wearing face mask 42. One approach to the positioning of the sensing piston and alarm circuit is to house such items in a module which is attached to a swivel connector which connects hose 34 to breathing regulator 40. Alternatively, the indicators may be incorporated into the breathing regulator. By positioning the light emitter and warning device in this position adjacent to or in the face mask, a He user is more readily enabled to perceive the warning devices. In addition, the position of the lights and warning devices so they may also be perceived outside the mask, enables a co-worker to perceive that such warnings are being given as well.

Figure 3:
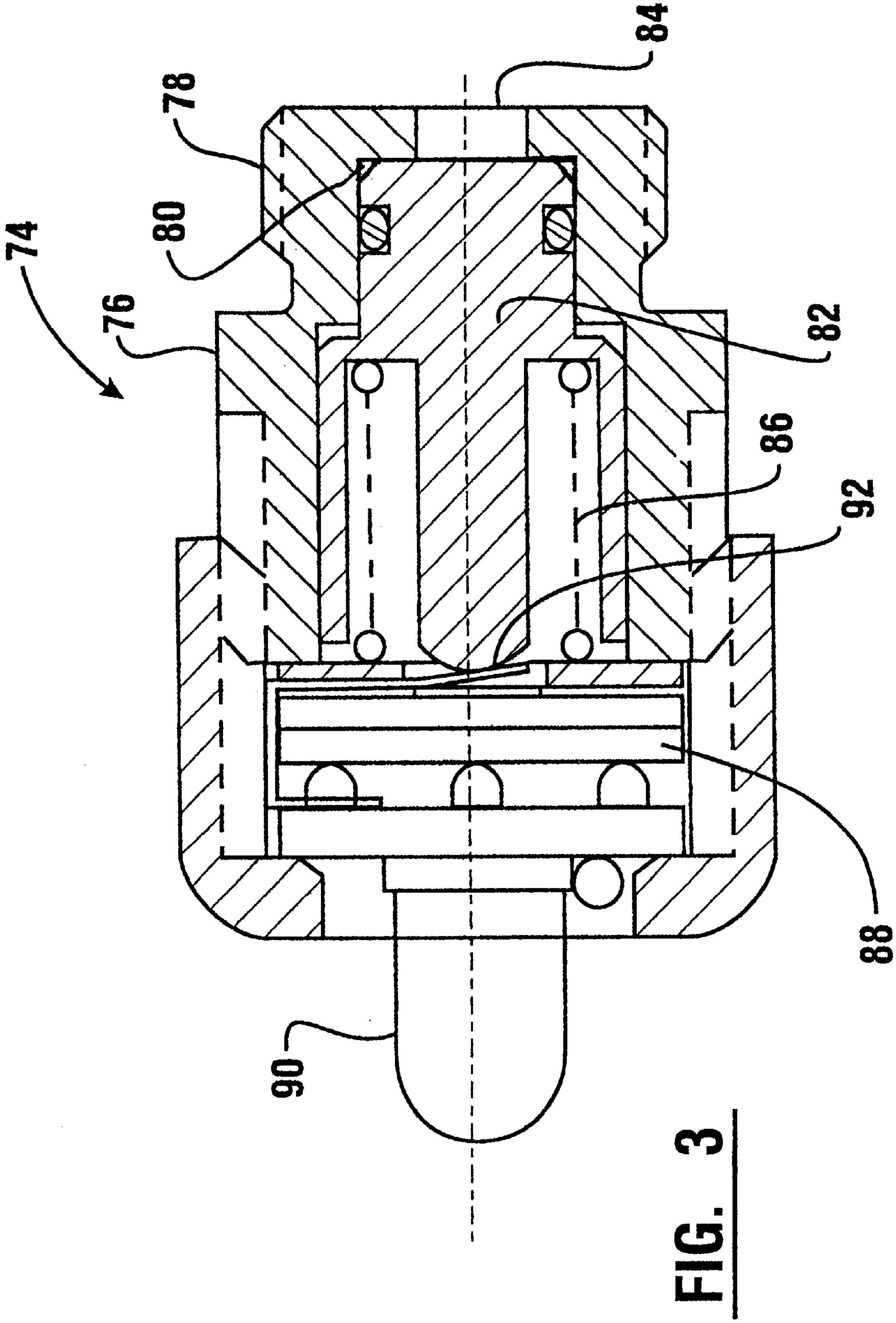
FIG. 3 is a cross sectional view of a device which incorporates a sensing piston and alarm circuit used in connection with the embodiment of the invention shown in FIG. 1.

A module shown in FIG. 3, generally indicated 74, is adapted for connection to a swivel connector. Module 74 includes a body 76 having a threaded end 78. Body 76 houses a sensing chamber 80 which has a sensing piston 82 movably mounted therein.

The same fluid pressure acting in hose 34 and regulator supply passage 54 shown in FIG. 1, is communicated to sensing chamber 80 through an opening 84. Fluid pressure communicated through opening 84 acts on sensing piston 82 tending to move it to the left as shown in FIG. 3. A spring 86 acts to oppose movement of the sensing piston in response to fluid pressure.

Module 74 includes a replaceable battery cell 88 or other energy source. Battery cell 88 is part of a circuit which includes one or more light emitting diodes, only one light emitting diode (LED) 90 being shown in FIG. 3. A spring loaded finger 92, which is engaged with a central projection on sensing piston 82, serves as a switch contact for completing the circuit which includes the light emitting diode 90 and the battery cell 88.

In the operation of module 74, when increased fluid pressure acting through opening 84 increases the biasing force of sensing piston 82 against switch finger 92, the alarm circuit is completed and LED 90 is illuminated.

In one preferred form of module 74, LED 90 is preferably made to flash on a periodic basis so as to attract the user's attention. Although module 74 as shown does not include further warning devices such as those discussed in connection with alarm circuit 64, it will be understood by those skilled in the art that such devices may be included in alternative embodiments.

Returning to the schematic view of the system shown in FIG. 1, the step up valve 24 includes a transfer piston 94 movably mounted therein. Transfer piston 94 bounds and separates three chambers or areas within step up valve 24. A first area 96 is shown positioned above the transfer piston 94 in FIG. 1. First area 96 is in fluid communication with a transfer passage 98. Transfer passage 98 is in fluid communication with regulator chamber 28 of pressure regulator 22, and is therefore at the regulator pressure.

Transfer piston 94 also bounds a second area 100 in step up valve 24. Second area 100 is open to atmosphere. A third area 102 is also bounded by transfer piston 94 in step up valve 24. Third area 102 is in fluid communication with supply conduit 20 and is exposed to the pressure from the pressure vessel 12.

Step up valve 24 further includes a vent valve generally indicated 104. Vent valve 104 includes a movable valve element 106 which is supported on a valve stem 108. Valve stem 108 includes an upper portion 109. In FIG. 1 upper portion 109 is shown engaged with a stop 107 which is positioned in fixed relation in an outlet passage 110 in step up valve 24.

Valve stem 108 extends through an opening in the transfer piston, which opening terminates at a vent valve seat 112. Vent valve seat 112 preferably comprises a resilient member and is sized for fluid tight engagement with valve element 106 when the valve element is positioned adjacent thereto.

Vent valve seat 112 extends in a wall which bounds a vent chamber 114 housed within the transfer piston 94. An outlet passage 116 extends from the vent chamber 114 inside transfer piston 94 to second area 100, which is open to atmosphere. A vent spring 118 is positioned in vent chamber 114 and acts on valve element 106. The biasing force of vent spring 118 acts to bias valve element 106 to engage vent valve seat 112.

Step up valve 24 further includes a transfer seat 120. Transfer seat 120 extends in surrounding relation to valve stem 108 and bounds outlet passage 110. Transfer seat 120 is engageable with a resilient member 122 which serves as a blocking member and which is supported on the transfer piston 94. Transfer seat 120 is shown in FIG. 1 in fluid tight engagement with resilient member 122. In this position fluid flow from first area 96 to outlet passage 110 is prevented.

Outlet passage 110 is operatively connected to a charging passage 124. Charging passage 124 is in communication with a charging chamber 126 on first stage regulator 22. A step up piston 127 is movably mounted in charging chamber 126. Step up piston 127 is in operative connection with bias spring 32 as shown. The bias spring serves as a connecting member operatively connecting the step up piston and the diaphragm. As previously discussed, the charging piston and spring serve as a force application device that opposes the pressure force acting on the diaphragm. The force of bias spring 32 against diaphragm 26 controls the pressure that is produced in regulator chamber 28 and which is supplied through the regulator outlet to breathing regulator 40. The movement of step up piston 127 in an upward direction in chamber 126 is limited by engagement of the piston with upper stops 129 as shown in FIG. 1.

The operation of the self contained breathing apparatus is now explained. When the pressure in pressure vessel 12 is at a suitably high level, the moveable transfer piston 94 in step up valve 24 which serves as a pressure sensor device, is in the position shown in FIG. 1. Transfer piston 94 is moved to this position by the pressure from the pressure vessel which is transmitted through the supply conduit 20 and acts on the surface of transfer piston 94 in third area 102 of the step up valve. A sufficiently high pressure in area 102 moves transfer piston 94 upward as shown as the force overcomes the force of the pressure in first area 96 acting on the larger area of the face of the transfer piston therein and vent spring 118. In this position transfer seat 120 is engaged with resilient member 122 in fluid tight relation. As a result, no air flows from first area 96 into the outlet passage 110.

In the position of the step up valve shown in FIG. 1, the vent valve 104 is open. This is due to upper portion 109 of the valve stem being engaged with the stop 107. The transfer piston 94 is positioned upward so that the valve element 106 is disposed away from vent valve seat 112. As a result, outlet passage 110 is in fluid communication with atmosphere through vent chamber 114, outlet passage 116 and second area 100. Because outlet passage 110 is at atmospheric pressure, charging passage 124 and charging chamber 126 are also at atmospheric pressure. This causes step up piston 127 to be disposed upwardly in the charging chamber 126 as shown in FIG. 1 against the upper stops 129.

In the position of the step up valve 24 shown in FIG. 1, the pressure in chamber 28 in the first stage pressure regulator 22 is determined based on the biasing force applied by spring 32 to the diaphragm 26 with the step up piston 127 in the stopped upward position. In one preferred form of the invention, this pressure is set to be at generally about 7.03 Kg./sq.cm (100 PSIG). As a result, air is supplied from the first stage regulator 22 to the breathing regulator 40 at about the 7.03 Kg./sq.cm (100 PSIG) level. In this condition, the pressure applied in sensing chamber 58 is insufficient to move sensing piston 60 to close switch contact 72. As a result, light emitter 68 and warning device 70 are not operative to provide indications to a user.

As the user continues use of the self contained breathing apparatus of the present invention, the pressure in the pressure vessel 12 which serves as the source of breathable air slowly falls. Eventually the pressure of the source reaches a level where it is desirable to give a user notice of impending depletion of the air supply. In one preferred form of the invention this point is set at about 25% of the initial fully charged pressure of the pressure vessel.

When the pressure in the pressure vessel 12 falls to a point where an indication is to be given to a user, the pressure in supply conduit 20 has correspondingly fallen. The pressure applied in third area 102 of the step up valve 24 is no longer sufficient to overcome the force applied by the pressure acting in first area 96 against the larger area of the upper face of the transfer piston 94. As a result, transfer piston 94 moves downwardly from the position shown in FIG. 1 to the position shown in FIG. 2. The transfer piston 94 is enabled to move downwardly because the generally 7.03 Kg./sq.cm (100 PSIG) pressure in first area 96 acting upon the large upper surface of transfer piston 94 produces a greater force in the downward direction than the upward force produced by the pressure in third area 102 acting on the smaller lower surface of the transfer piston. Second area 100, which is indicated by the area underneath the transfer piston 94, is open to atmosphere to enable the transfer piston to more readily move between the positions shown in FIGS. 1 and 2.

Figure 2:
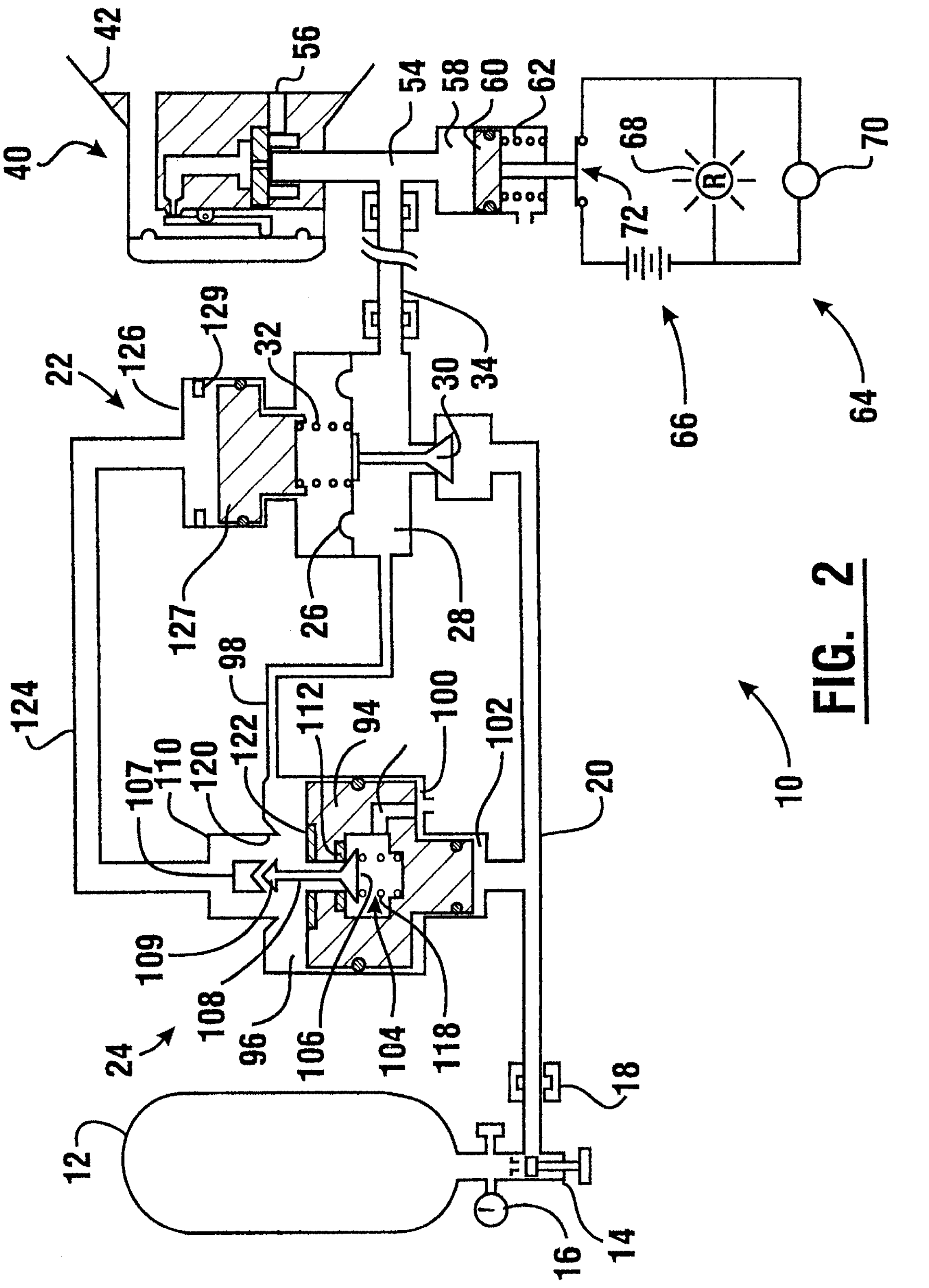
FIG. 2 is a schematic view similar to FIG. 1 in which the air supply has reached a level indicative of impending depletion.

In the position of transfer piston 94 shown in FIG. 2 the resilient member 122 is disposed away from the transfer seat 120. This enables fluid to flow from the first area 96 in the transfer valve to the outlet passage 110 and into the charging passage 124. Flow to atmosphere from the outlet passage 110 is prevented because the vent valve 104 is closed. Vent valve 104 is closed by the force of spring 118 acting on valve element 106. Valve element 106 engages valve seat 112 as valve stem 108 disengages stop 107.

The pressure in regulator chamber 28, which initially is generally about 7.03 Kg./sq.cm (100 PSIG), is transmitted through the transfer passage 98 to the first area 96 of the step up valve. When the transfer valve moves to the condition shown in FIG. 2, this pressure is transmitted through the outlet passage 110 of the step up valve and into the charging passage 124. This pressure in the charging passage is transmitted to the charging chamber 126 on first stage pressure regulator 22. This increased pressure in the charging chamber moves step up piston 127 in a downward direction from that shown in FIG. 1 until the step up piston engages a lower stop. This movement of step up piston 127 causes biasing spring 32 to apply increased force to diaphragm 26. This increases the regulator pressure in chamber 28 as well as the pressure supplied to breathing regulator 40 through hose 34.

In one preferred form of the invention, the travel of step up piston 127 is limited to a maximum distance which increases the biasing force of spring 32 a controlled amount. This controlled amount causes the pressure in chamber 28 to rise from the original level, which is approximately 7.03 Kg./sq.cm (100 PSIG), to approximately 10.55 Kg./sq.cm (150 PSIG).

The increased pressure in hose 34 is transmitted to the regulator supply passage 54 in the breathing regulator 40. This causes a conventional or unconventional valve and whistle combination or a vibrating device housed within the breathing regulator to begin providing an indication to the user that the air supply is approaching depletion. The increased pressure is also applied to sensing chamber 58. This increased pressure in sensing chamber 58 also moves the sensing piston 60 against the force of spring 62. The movement of piston 60 closes switch contacts 72 which activates the light emitter 68 and the warning device 70 in alarm circuit 64.

As previously discussed, because the light emitter 68 and warning device 70 are preferably positioned to be perceived by the user wearing mask 42, this increases the probability that user will perceive the multiple indications being given that the air supply is approaching depletion. The user knows to begin moving out of the area of the noxious atmosphere to an area of breathable air in which the pressure vessel 12 may be replaced with a new air supply or otherwise replenished. In addition, if the devices 68 and 70 are mounted adjacent to a swivel which attaches hose 34 to the breathing regulator 40, or are otherwise perceivable outside the mask, individuals working with the user of face mask 42 will also be alerted that the user's air supply is approaching depletion. Thus, if for some reason a user fails to note the multiple warnings being given, others may advise the user of the need to leave the area.

It should be noted that the step up valve 24 and step up piston 127 will remain in the position shown in FIG. 2 for as long as the pressure vessel 12 is being used, the breathing regulator 40 is connected and there is sufficient pressure. If the pressure vessel 12 is replaced with a new fully charged vessel, the step up valve 24 will initially maintain the position shown in FIG. 2. This is because the transfer piston will be in a downward position having been in that position when the pressure in pressure vessel 12 and conduit 20 were depleted, or alternatively when valve 14 was closed and the pressure in conduit 20 was depleted. When a higher pressure is again applied, such as when a fully charged pressure vessel is connected to conduit 20 and valve 14 is opened, pressure in regulator chamber 28 is initially transmitted through transfer passage 98 and first area 96, to the charging passage 124. As a result, the step up piston 127 is moved downward, causing the first stage regulator to be set at approximately 10.55 Kg./sq.cm (150 PSIG). As a result the alarm circuit will give an indication that it is working.

A few seconds after the fully charged pressure vessel has been connected to conduit 20 the high pressure acting in third area 102 on the face of transfer piston 94 overcomes the 10.55 Kg./sq.cm (150 PSIG) pressure force acting on the opposed larger face of the transfer piston in first area 96. The high pressure acting in area 102 moves the transfer piston 94 in an upward direction from the position shown in FIG. 2, and returns the transfer piston to the position shown in FIG. 1.

As the transfer piston returns to the position shown in FIG. 1 the pressure in the charging passage 124 is relieved to atmosphere by the vent valve 104 through second area 100. The return of the charging passage 124 and charging chamber 126 to atmospheric pressure causes step up piston 127 in regulator 22 to return to its upward position against the upper stops 129. Regulator 22 returns to supplying air at approximately 7.03 Kg./sq.cm (100 PSIG). The alarm circuit 64 no longer provides an alarm indication because spring 62 is sufficiently strong to move the sensing piston 60 against the pressure force and the circuit is no longer completed. The apparatus will continue to supply air at this pressure until the pressure in the substitute pressure vessel reaches the point where an indication of impending depletion is to be given or valve 14 is closed.

Furthermore, in an exemplary embodiment of the invention the apparatus may be viewed as having a first movable member (26), a second chamber (126), a second movable member (127), a third chamber (102), a third movable member (94), a third surface area (lower outer surface area of the third movable member), a fourth chamber (96), a fourth movable surface (upper outer surface of the third movable member), a fifth chamber (100), and a connecting device (32).

Figure 4:
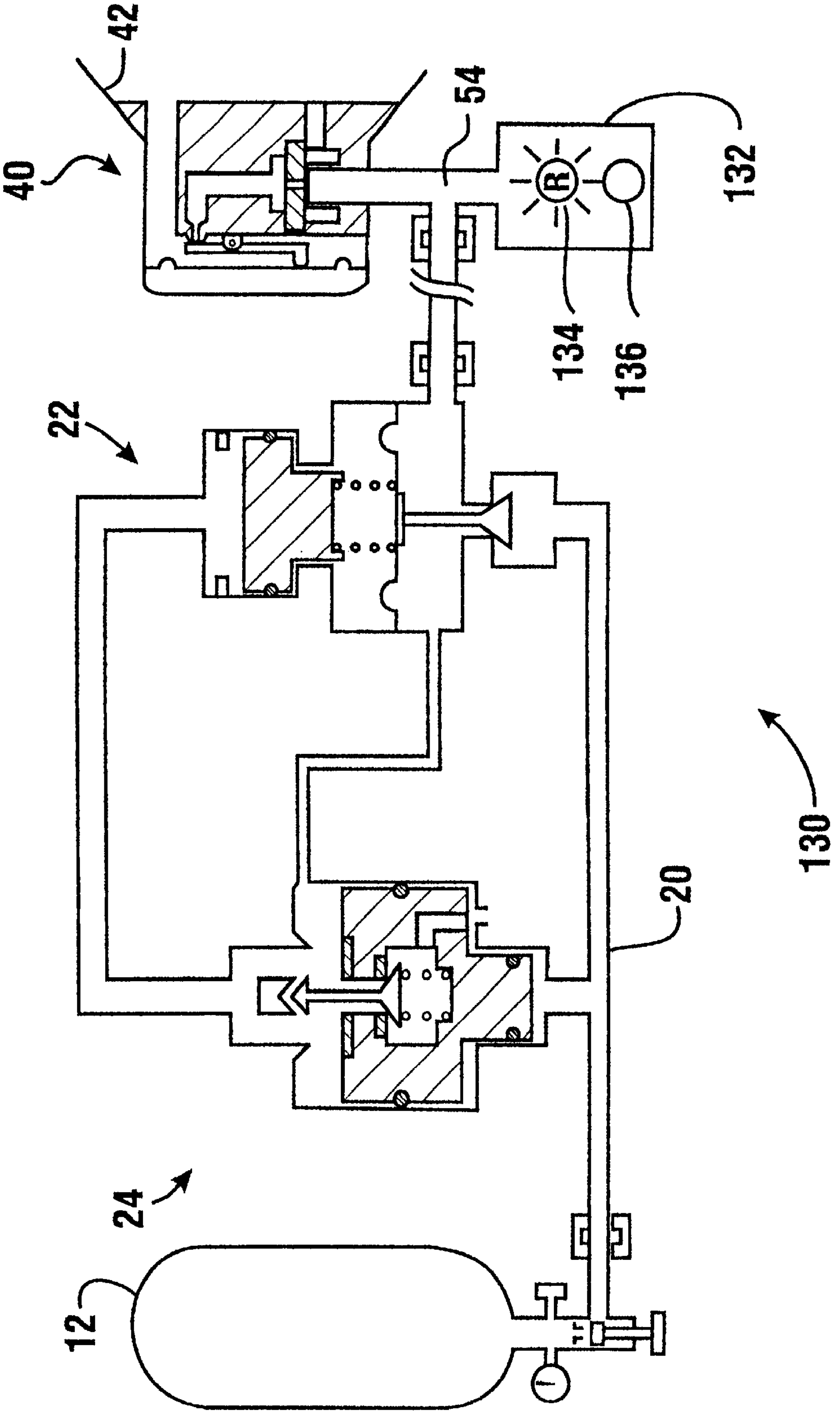
FIG. 4 is a schematic view of an alternative embodiment of a self contained breathing apparatus of the present invention.

An alternative embodiment of the self contained breathing apparatus, generally indicated 130, is schematically shown in FIG. 4. This alternative embodiment is identical in all respects to the first embodiment except as otherwise noted. In this embodiment of the invention, the sensing chamber, the sensing piston and alarm circuit is replaced with an electronic alarm module generally indicated 132. Electronic alarm module 132 preferably includes a battery or other power source suitable for actuating indicating devices such as a light 134 or a piezoelectric sound emitter 136. Of course other types of indicating devices may also be a part of electronic alarm module 132.

Unlike the previous embodiment, electronic alarm module 132 includes a semiconductor pressure sensor which is in fluid communication with regulator supply passage 54 and hose 34. This semiconductor pressure sensor is in operative connection with a sensing circuit operative to actuate the indicators 134 and 136 responsive to the increase in pressure substantially above 7.03 Kg./sq.cm (100 PSIG) responsive to the operation of step up valve 24.

In addition to actuating the indicators 134 and 136, electronic alarm module 132 also includes a clock device which is operative to provide a timing function and to control the operation of the indicating devices in response to elapsed time since the step up in pressure. For example, the frequency at which light 134 is flashed may be changed by the circuitry as time passes from when the pressure was initially stepped up. The frequency of such flashing may provide an indication to a user as to how long it has been since the low air supply indication was given. This may be advantageous where a user is operating in situations where it is difficult to sense how much time has elapsed. The alarm module may also include programmed logic to defer initiating the timing function in response to a pressure increase of short duration such as when a new pressure vessel is first installed.

The circuitry may operate warning indicator 136 to modify the type of indication given depending on the period of time since the increased regulator pressure indicative of falling source pressure was sensed. This indication may include for example a change in color of a bi-color LED or a change in pitch produced by a piezoelectric emitter. Alternatively, electronic alarm module 132 may further include a processor, programmable memory and an emitter which produce human voice emulation indicative of the time since the stepped up pressure was sensed. This may provide a user with a periodic voice indication as to how long it has been since the increased pressure indicating impending depletion of the air supply was given. These voice indications, which are preferably periodically given, update the user as to how long it has been since an initial warning was provided.

In alternative embodiments, the electronic alarm module may include a voice emulation or other indication to the user which provides an estimate of the amount of time remaining in the air supply. This may be based on a pre-programmed estimate data stored in a memory or alternatively may be based on measurement of various quantities within the system. Because in the preferred embodiment of the invention the installation of a new pressure vessel provides a short period of elevated pressure, this may be used as a time reference for purposes of the electronic circuitry in the electronic alarm module. For example, the electronic alarm module may begin measuring an elapsed time with its clock device from the initial pressure indication given at the time of replacement of pressure vessel 12. Based on the elapsed time that it has taken to deplete the available air in the supply to a point where pressure step up again occurs, the processor in the electronic alarm module 132 may calculate an estimate of how much longer the air supply will last based on the overall rate of depletion. This calculation may be used to provide a user with an indication of the time remaining through the indicating devices.

Alternatively, more sophisticated schemes may be programmed into the electronic alarm module to attempt to provide a more accurate estimate of the amount of time remaining. Such alternative embodiments may measure the variation in pressure which results upon delivery of air through the breathing regulator 40 and the duration of such pressure fluctuations. From this information and preprogrammed parameters which correlate the amount of air being used with such pressure fluctuations, the electronic alarm module may be programmed to calculate a value indicative of the amount of time remaining at current consumption rates. Thereafter an indication of such time may be given through the sound emitter or another indicator. Alternatively, the variation in pressure in the pressure vessel measured in conduit 20, as a function of time may be used to estimate consumption rates and/or available time remaining.

Of course in other embodiments other approaches may be used. The particular approach taken will depend on the needs and the particular application in which the system will be used and will be provided with the understanding that no system will be able to indicate to a user exactly how long the system may be operated before the user runs out of air.

The use of an electronic alarm module 132 which provides an indication external of the mask as to the elapsed time since the pressure was increased and/or an estimate of the amount of time remaining, enables others in proximity to the user to perceive such indications. Where indications are given by way of light emitters or sound emitters, nearby users will be able to perceive the condition of the user's air supply. This may be important, for example, in situations where a user has suffered an injury or has lost consciousness and is unable to advise others as to how long the air supply is likely to last. In addition, an electronic alarm module 132 may include infrared emitters, sound emitters, RF emitters, electronic emitters or similar non visible, non audible signal emitters which enable information to be read therefrom using a connector or receiver placed adjacent thereto. Of course the processor in the electronic alarm module may be programmed to provide numerous types of information transfer, as well as on board diagnostic information, depending on the needs of the system.

It should be understood that while in the embodiments shown the first stage regulator, step up regulator and indicator are shown schematically as separate units, in embodiments of the invention some or all of such components may be arranged together within a single housing. Alternatively some or all of such components may be combined in housings with other components of the system. The various arrangements of the components shown schematically are all within the scope of the present invention.

Thus the new self contained breathing apparatus of the present invention achieves the above stated objectives, eliminates difficulties encountered in the use of prior devices and systems, solves problems and attains the desirable results described herein.

In the foregoing description certain terms have been used for brevity, clarity and understanding. However no unnecessary limitations are to be implied therefrom because such terms are for descriptive purposes and are intended to be broadly construed. Moreover the descriptions and illustrations herein are by way of examples and the invention is not limited to the exact details shown and described.

Further, in the following claims any feature that is described as a means for performing a function shall be construed as encompassing any means known in the art which is capable of performing the recited function and shall not be deemed limited to the particular means shown in the foregoing description performing the function, or mere equivalents thereof.

Having described the features, discoveries and principles of the invention, the manner in which it is constructed and utilized, and the advantages and useful results attained; the new and useful structures, devices, elements, arrangements, parts, combinations, systems, equipment, operations, methods and relationships are set forth in the appended claims.

I claim:

1. Apparatus adapted to be positioned fluidly intermediate of a source of breathable air and a breathing regulator for delivering air to a user, comprising:

- a regulator chamber adapted for fluid communication with both the source and the breathing regulator;
- a first movable member bounding the regulator chamber, wherein the first movable member moves responsive to a regulator pressure in the regulator chamber;
- a metering member operatively connected to the first movable member, wherein the metering member is operative to control air flow from the source into the regulator chamber responsive to movement of the first movable member;
- a second chamber;
- a second movable member bounding the second chamber and movable responsive to a second pressure therein;
- a connecting device operatively connecting the second movable member to the first movable member; and
- a valve mechanism in operative connection with the second chamber, wherein the valve mechanism is adapted for operative connection with the source, wherein the valve mechanism is operative to vary the second pressure responsive to a source pressure of the source, wherein the second pressure is varied to move the second movable member responsive to a reduction in the source pressure and such movement of the second movable member is operative to increase the regulator pressure.

2. The apparatus according to claim 1 wherein the valve mechanism is operative to connect the second chamber to atmospheric pressure when the source pressure is above a pressure level and to elevate the second pressure above atmospheric pressure when the source pressure is below the pressure level.

3. The apparatus according to claim 2 wherein when the source pressure is below the pressure level the valve mechanism is operative to place the second chamber in a fluid communication with the source.

4. The apparatus according to claim 1 wherein the valve mechanism comprises a third chamber, and a third movable member movably mounted in the third chamber, and wherein the third movable member moves responsive to a third pressure in the third chamber, wherein the third pressure varies in correspondence with the source pressure, and wherein the third movable member moves responsive to the reduction in source pressure, and such movement of the third movable member is operative to vary the second pressure to increase the regulator pressure.

5. The apparatus according to claim 4 wherein movement of the third movable member responsive to the reduction in source pressure is operative to increase the second pressure.

6. The apparatus according to claim 4 wherein movement of the third member responsive to the reduction in source pressure is operative to cause the regulator chamber to be operatively connected to the second chamber.

7. The apparatus according to claim 6 and further comprising a fourth chamber bounded by a fourth movable surface, and wherein the fourth chamber is in operative connection with the regulator chamber and wherein the fourth surface is in operative connection with the third movable member, and wherein when the fourth surface is in a first position the fourth chamber is fluidly separated from the second chamber and when the fourth surface is in a second position the fourth chamber and the second chamber are in fluid communication, and wherein the reduction in source pressure is operative to move the third movable member such that the fourth surface moves to the second position.

8. The apparatus according to claim 7 and further comprising a vent valve, wherein the vent valve is operative to vent the second chamber to atmosphere responsive to the fourth surface moving to the first position.

9. The apparatus according to claim 7 wherein the third movable member has a third surface area acted on by the third pressure in the third chamber to produce a third force, and the fourth surface has a fourth surface area acted on by the regulator pressure in the fourth chamber to produce a fourth force, and wherein the valve mechanism is operative to cause the fourth surface to move to the second position responsive to the third force and the fourth force having a predetermined relationship.

10. The apparatus according to claim 9 wherein the fourth surface moves to the second position when the fourth force exceeds the third force.

11. The apparatus according to claim 9 wherein the third movable member comprises a transfer piston, and the third surface and fourth surface are generally opposed surfaces of the transfer piston.

12. The apparatus according to claim 11 and further comprising a vent valve mounted on the transfer piston, wherein when the fourth surface is in the first position the second chamber is in fluid communication with atmosphere through the transfer piston, and wherein when the fourth surface is in the second position the vent valve prevents air flow therethrough.

13. The apparatus according to claim 12 and further comprising a fifth chamber, wherein the fifth chamber is bounded by the transfer piston, and wherein the fifth chamber is in operative fluid connection with atmosphere and the vent valve, wherein in the open position of the vent valve the second chamber is in fluid communication with atmosphere through the fifth chamber.

14. The apparatus according to claim 1 wherein the valve mechanism is operative to fluidly connect the regulator chamber to the second chamber responsive to the source pressure falling to a pressure level.

15. The apparatus according to claim 1 wherein the connecting device includes a spring.

16. The apparatus according to claim 15 wherein the second movable member moves responsive to the reduction in source pressure to bias the first movable member to admit air past the metering member and into the regulator chamber.

17. The apparatus according to claim 16 wherein the second chamber includes a stop, and wherein the valve mechanism is operative responsive to the reduction in source pressure to increase pressure in the second chamber sufficiently to move the second member against the force of the spring and to engage the stop.

18. The apparatus according to claim 1 and further comprising an indicator in operative connection with the regulator pressure, and wherein the indicator is operative to indicate the increase in regulator pressure.

19. The apparatus according to claim 18 wherein the indicator is operative to indicate an elapsed time since the increase in regulator pressure.

20. The apparatus according to claim 18 wherein the indicator is operative to indicate a time that air is expected to be available from the source.

21. The apparatus according to claim 18 wherein the indicator is perceivable by others in addition to the user.

22. The apparatus according to claim 21 wherein the indicator includes a nonvisible, nonaudible signal emitter.

23. Apparatus adapted to be positioned fluidly intermediate of a source of breathable air and a breathing regulator for delivering air to a user, comprising:

a first stage regulator, adapted for fluid communication with the source and the breathing regulator, the first stage regulator including a movable member, wherein the movable member is acted upon by a pressure force of air delivered from the source, and wherein the first stage regulator further includes a force application device in operative connection with the movable member, wherein the force application device is operative to oppose the pressure force acting on the movable member, and wherein the force of the force application device acting on the movable member is operative to control a regulator pressure at an outlet of the first stage regulator, the outlet being adapted for operative connection to the breathing regulator;

a source pressure sensor device, adapted for sensing a source pressure of the source, wherein the pressure sensor device is operatively connected to the force application device, and wherein the source pressure sensor is operative to change the force applied by the force application device to increase the regulator pressure in response to the pressure sensing device sensing a reduction in the source pressure.

24. The apparatus according to claim 23 wherein the force application device includes a charging chamber and a charging piston bounding the charging chamber, the charging piston movably mounted in the charging chamber, wherein movement of the charging piston is operative to change the force acting to oppose the pressure force on the movable member, and wherein the source pressure sensor device is in operative connection with an air delivery device, and wherein the air delivery device is operative to deliver air into the charging chamber to move the charging piston responsive to the reduction in source pressure.

25. The apparatus according to claim 23 wherein the pressure sensor device includes a transfer valve, wherein the transfer valve includes a transfer piston, a first chamber and a second chamber, wherein the transfer piston is movably mounted relative to the first and second chambers, and wherein the transfer piston includes a first surface area in the first chamber acted upon by the source pressure and a second surface area in the second chamber acted upon by the regulator pressure, and wherein the second surface area is greater than the first surface area, and wherein the force of the force application device changes responsive to the transfer piston moving from a first position to a second position relative to the first and second chambers when a transfer force produced by the regulator pressure acting on the second surface area exceeds an opposing force produced by the source pressure acting on the first surface area.

26. The apparatus according to claim 25 wherein the force application device includes a charging chamber and a charging piston movably mounted in and bounding the charging chamber, and wherein movement of the charging piston is operative to change the force applied by the force application device acting to oppose the pressure force acting on the movable member, and wherein the second chamber of the transfer valve further is in operative connection with a valve seat and the transfer valve further includes a blocking member in operative connection with the transfer piston, wherein the valve seat includes an opening and the opening is in fluid communication with the charging chamber, and wherein when the transfer piston is in the first position the blocking member is adjacent the valve seat to restrict air flow from the second chamber to the charging chamber, and wherein in the second position of the transfer piston the blocking member is disposed from the valve seat to enable air flow from the second chamber to the charging chamber, wherein the air flow to the charging chamber moves the charging piston to increase the regulator pressure.

27. The apparatus according to claim 26 and further comprising an outlet passage, wherein the opening in the valve seat is connected to the charging chamber through the outlet passage, and further comprising a stop in the outlet passage, and further comprising a vent passage through the transfer piston, wherein the vent passage is operatively connected to atmosphere, and further comprising a vent valve in the vent passage, wherein the vent valve selectively enables air flow therethrough, and wherein the vent valve is in operative connection with an actuating member, wherein in the first position of the transfer piston the vent valve and the stop are operatively engaged by the actuating member wherein the vent valve is open, whereby the charging passage is open to atmosphere, and wherein in the second position of the transfer piston the vent valve is operatively disengaged from the stop, wherein the vent passage is closed.

* * * * *